United States Patent [19]

Wanderer et al.

[11] Patent Number: 4,878,902
[45] Date of Patent: Nov. 7, 1989

[54] NEEDLE GUARD FOR BODY SUBSTANCE ISOLATION

[76] Inventors: Alan A. Wanderer, 1075 E. Radcliffe, Englewood, Colo. 80110; William E. Sagstetter, 2217 E. Grove, Denver, Colo. 80210

[21] Appl. No.: 160,150

[22] Filed: Feb. 25, 1988

[51] Int. Cl.$^4$ ............................................. A61M 5/32
[52] U.S. Cl. .................................... 604/192; 604/263
[58] Field of Search ............... 604/192, 198, 164, 187, 604/110, 263

[56] References Cited

U.S. PATENT DOCUMENTS

| | | | |
|---|---|---|---|
| 4,695,274 | 9/1987 | Fox | 604/198 |
| 4,731,059 | 3/1988 | Wanderer et al. | 604/192 |
| 4,778,453 | 10/1988 | Lopez | 604/110 |
| 4,782,841 | 11/1988 | Lopez | 604/164 |

*Primary Examiner*—John D. Yasko
*Attorney, Agent, or Firm*—Cahill, Sutton & Thomas

[57] ABSTRACT

A non-rotatable axially translatable anterior guard exposes, upon posterior translation along a needle supporting hub, the anterior end of the needle ready for use. Upon anterior translation of the anterior guard, it lockingly engages the hub to retain the needle therein. A detachable tab creates an aperture in the anterior guard for exteriorizing the needle and upon attachment seals the aperture to isolate within the anterior guard, in combination with the fit between the hub and the anterior sleeve, any body substances remaining with the needle after use. A removable posterior guard encloses the posterior end of the hub to receivingly retain any body substances remaining therewith after use of the needle. The anterior and posterior guards, in combination with sealing tape, permit sterilizing the needle prior to use and isolating there within any body substances after use.

21 Claims, 8 Drawing Sheets

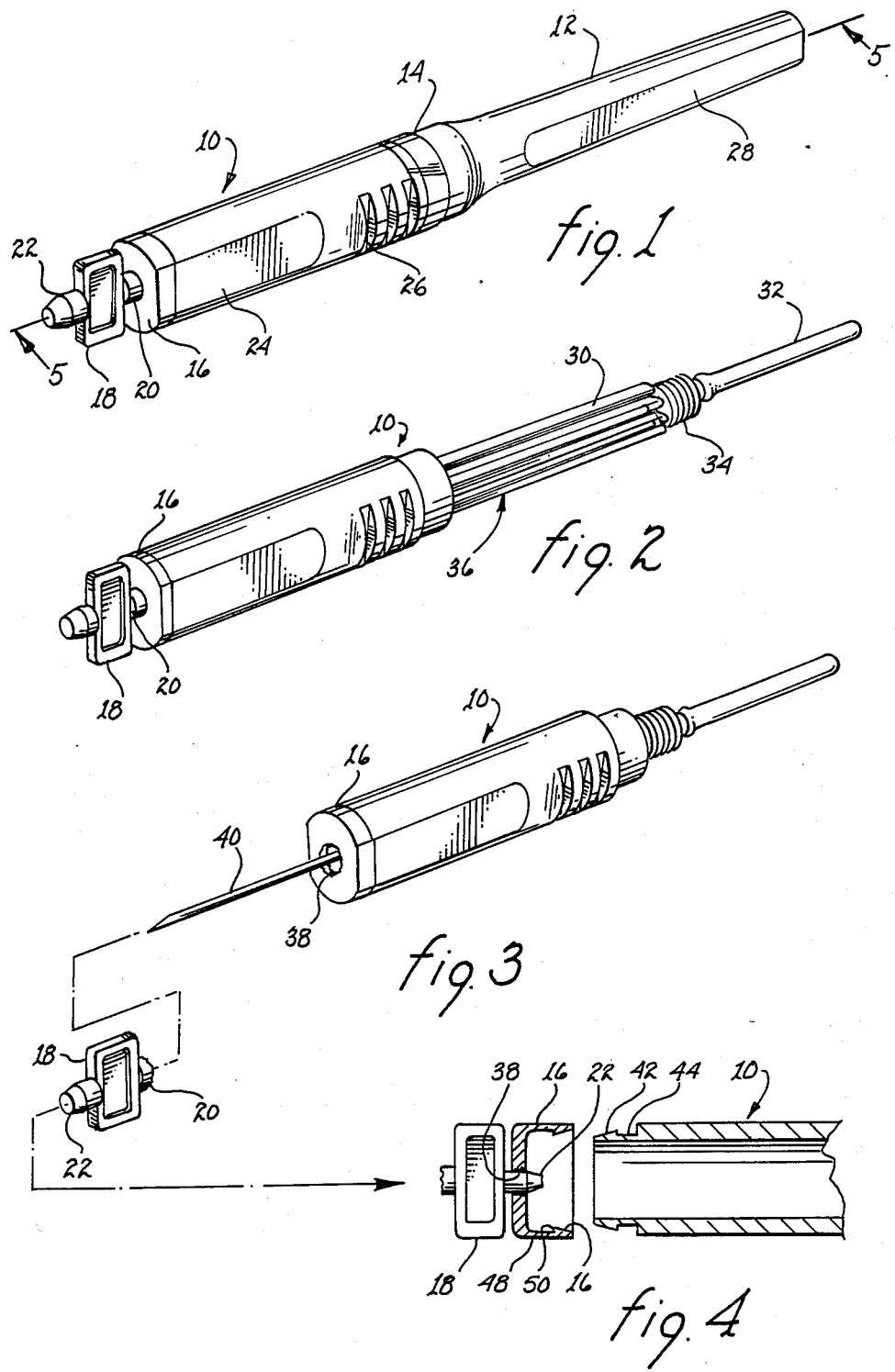

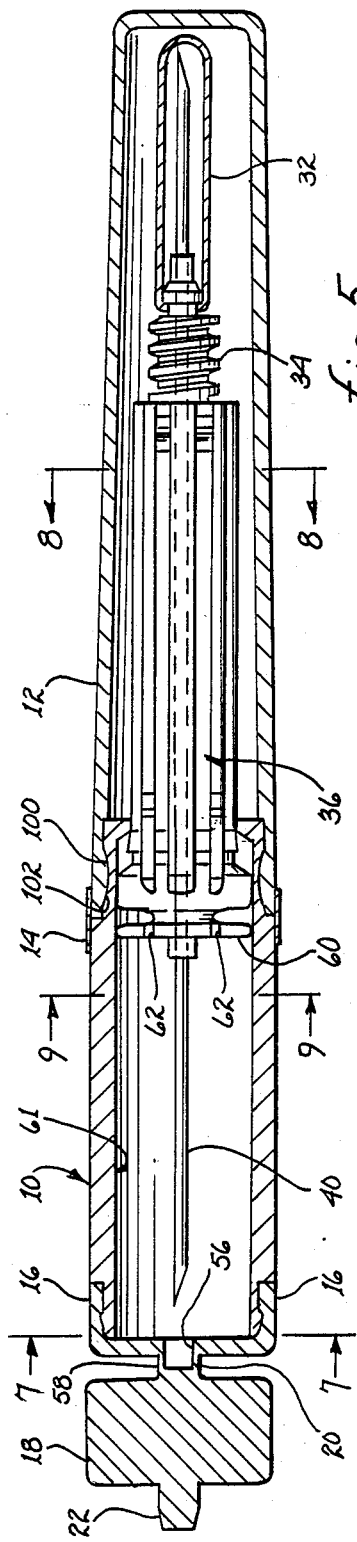

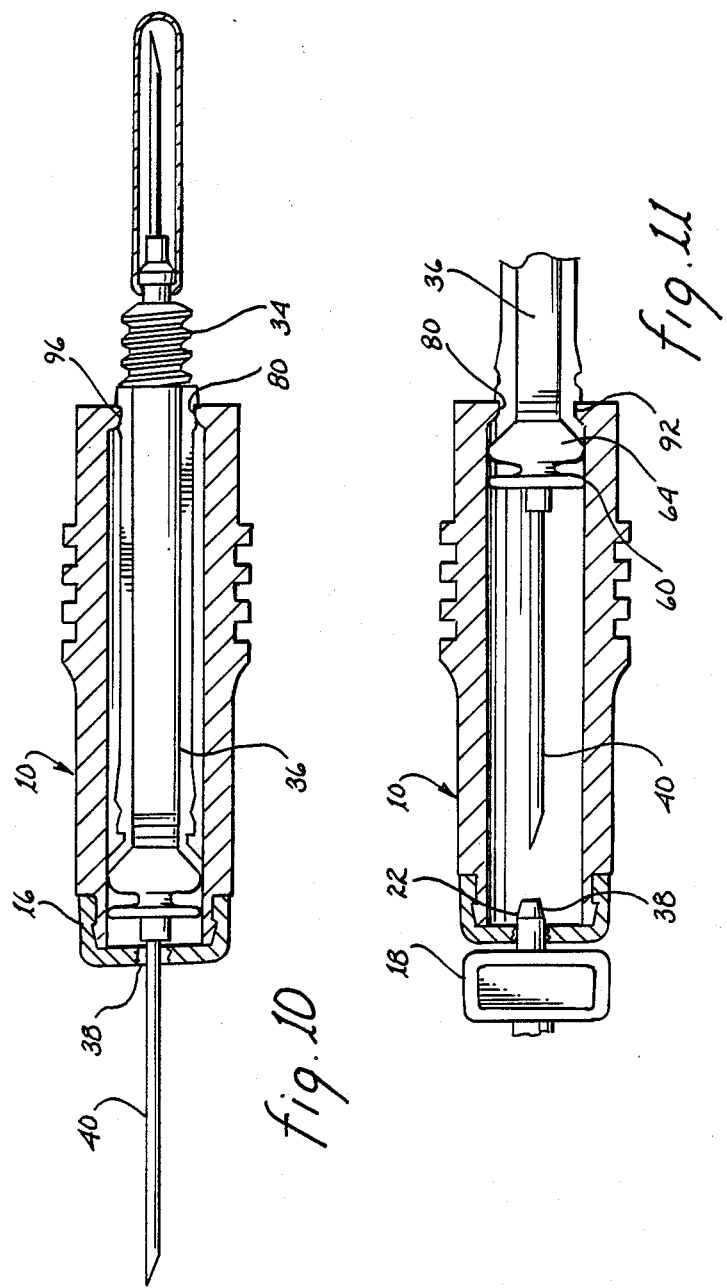

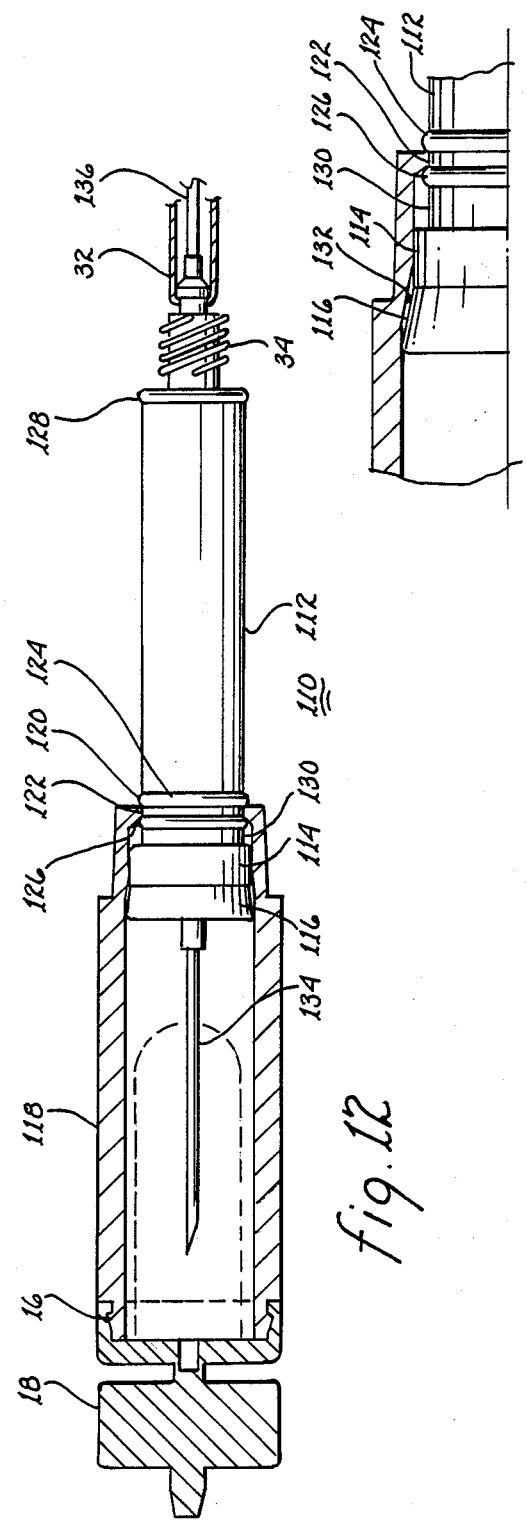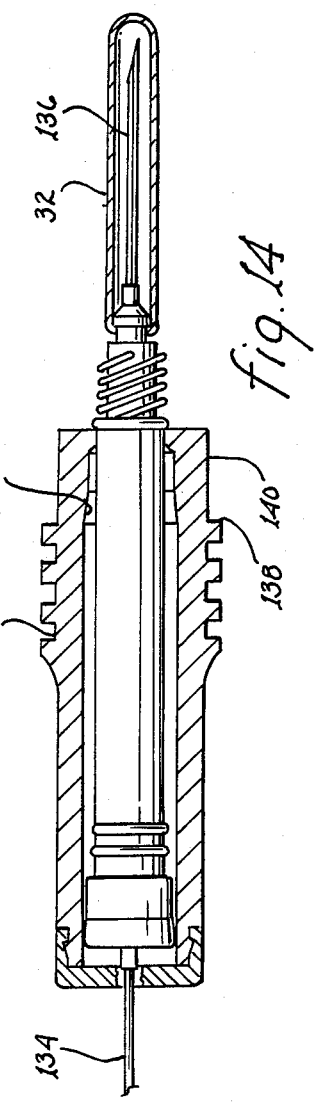

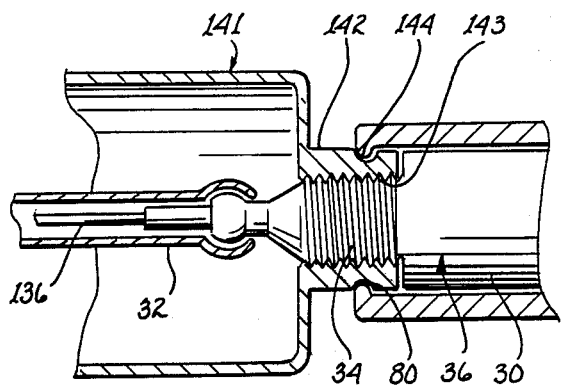
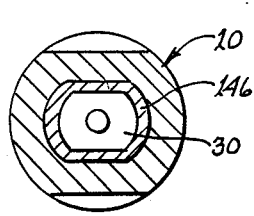
fig. 15 fig. 17
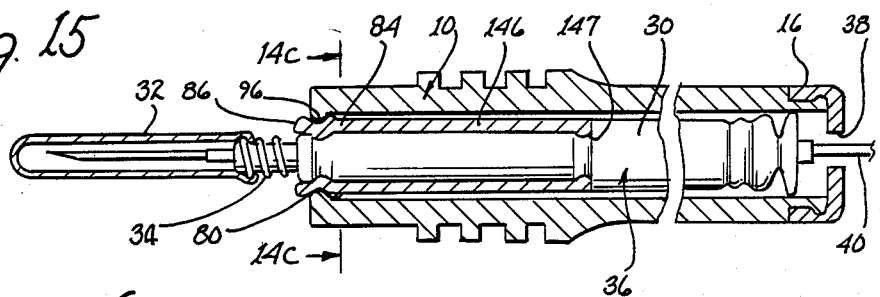
fig. 16
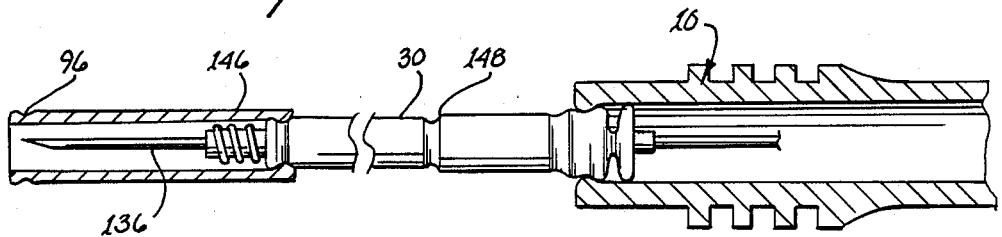
fig. 18
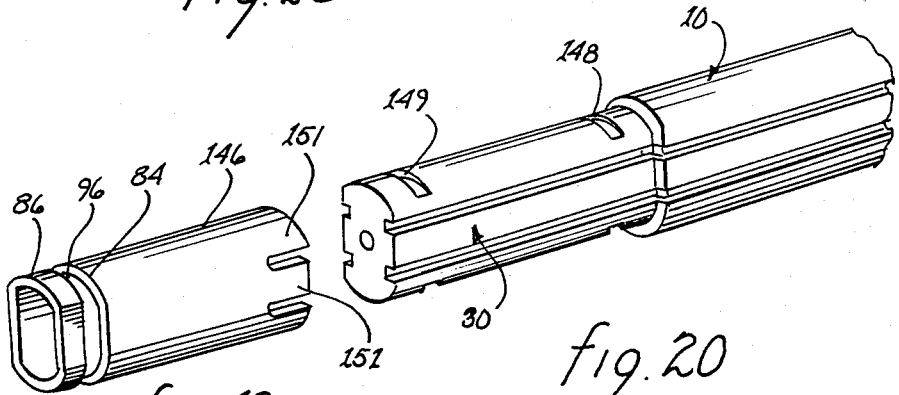
fig. 19 fig. 20

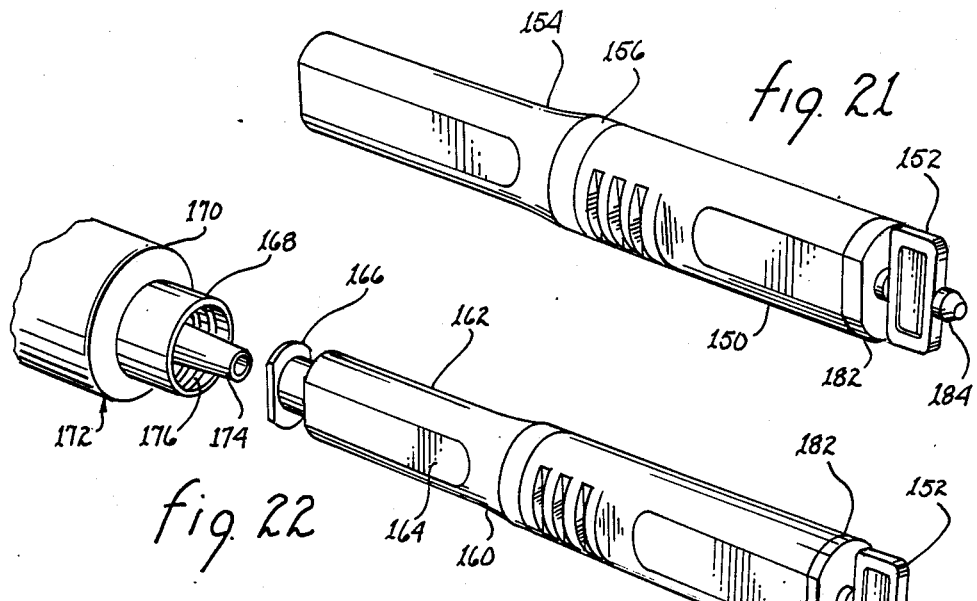
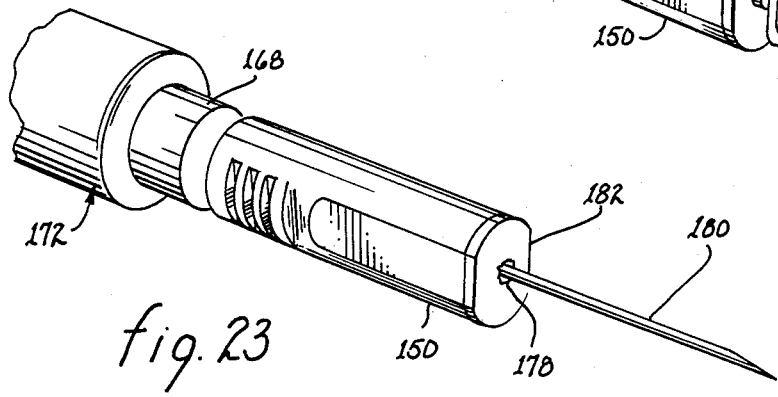
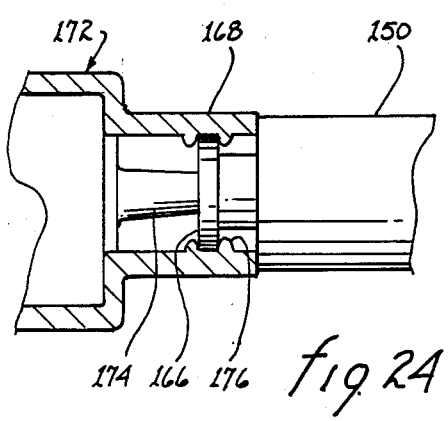

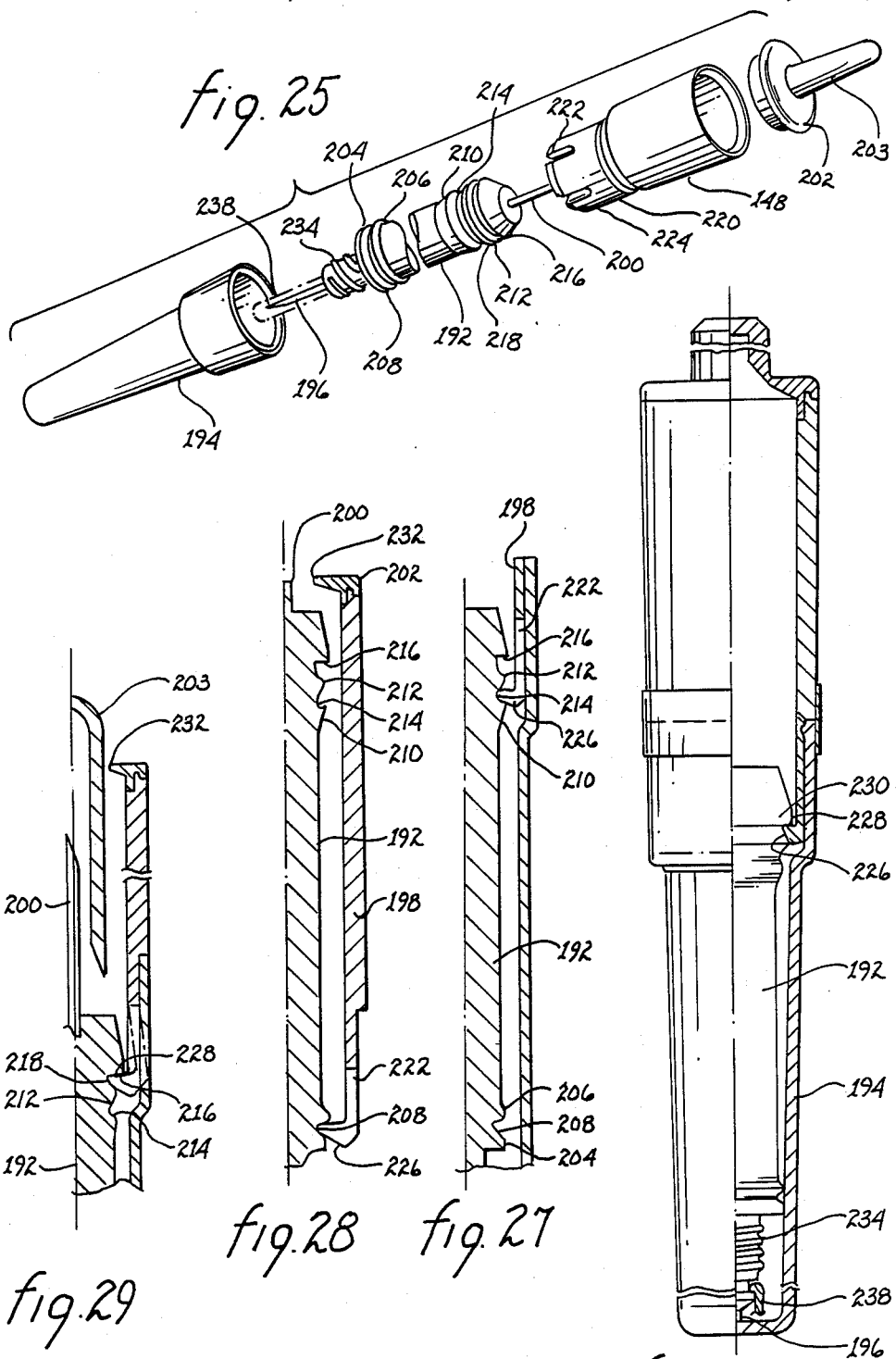

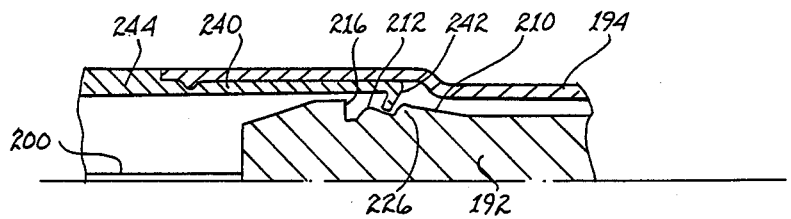
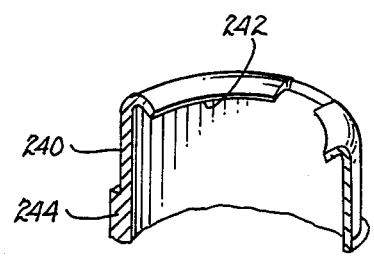
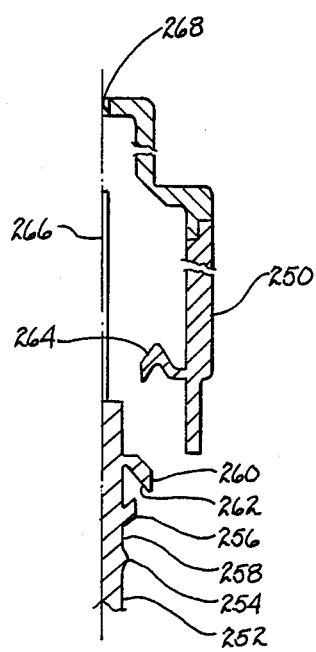
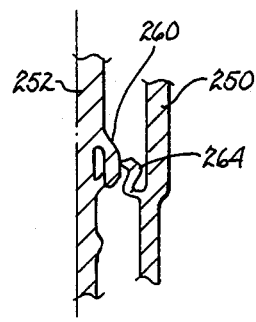
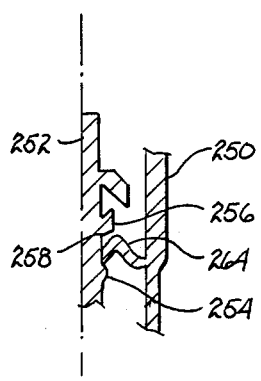
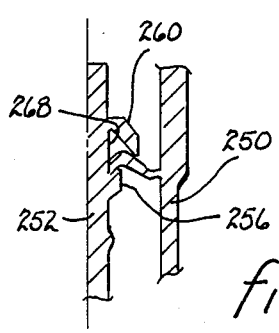

NEEDLE GUARD FOR BODY SUBSTANCE ISOLATION

REFERENCE TO RELATED APPLICATIONS

The invention described in this application is related to the invention described in a PCT application, entitled "Needle Guard", filed on May 14, 1987 and assigned Ser. No. PCT/US87/01140, which invention was invented by the present inventors.

BACKGROUND OF THE INVENTION

1. Field of the Invention

The present invention relates to a guard device for needles used in medical practice and, more particularly, to guard devices for single and double ended needles.

2. Description of the Prior Art

A needle shield which must be removed anteriorly from a needle hub before a syringe can be used for a medical procedure is well known. Remounting such a shield requires a user to insert the point of the needle into the open end of the shield and draw the shield posteriorly over the needle until it engages the needle. Such a removable needle shield contains several limitations, including: (1) after a liquid medicament has been drawn up in a syringe, medical personnel may occasionally delay the administration of the medicament, which delay requires retrieval and replacement of the needle shield to prevent contamination of the sterile needle and creates extra steps for busy medical personnel; (2) medical personnel often remove this needle shield by holding the needle shield between their teeth or lips. This practice has been associated with accidental self-puncture in the face or other body parts; (3) in order to recover a used needle with a previously removed needle shield, it is necessary to replace the needle shield back over the pointed end of the used needle, which replacement increases the risk to medical personnel of accidentally puncturing themselves with the pointed end of the used needle; and, (4) if the needle has been accidentally bent during a medical procedure or if the needle shield is replaced over the needle at an incorrect angle, the needle point may inadvertently pierce the side of the needle shield and puncture the fingers or hand.

In order to avoid problems attendant needle shields which must be remounted posteriorly from a location anterior of the needle point, various devices have been developed. U.S. Pat. No. 4,573,976 describes a shield translatably mounted upon the barrel of a hypodermic syringe which need not be threaded onto the needle upon remounting. A flexible projection or the like extending from an attachment to the syringe barrel lockingly engages the sleeve after it has been translated anteriorly to the lock position. U.S. Pat. No. 4,592,744 is directed to a device for enclosing either a single needle or a double ended needle by translating the needle posteriorly into a holder. Such translation may be effected by drawing the barrel of a syringe attached to a single needle posteriorly or by drawing the collection tube penetrably engaged with the posterior needle of a double ended needle posteriorly. U.S. Pat. No. 4,643,199 illustrates a collection tube having apparatus disposed at the anterior end thereof for selectively translating a double ended needle into a collection tube holder. U.S. Pat. No. 4,650,468 illustrates an anterior enclosure for the needle of a hypodermic syringe, which needle is drawn past a sealing member that scrapes body substances off the needle during retraction and permits exposure to such wiped body substances. U.S. Pat. No. 4,666,435 describes a shield usable in conjunction with the barrel of a hypodermic needle for translation anteriorly to enclose the needle therein. U.S. Pat. No. 4,675,005 is directed to a disposable syringe having a piston rotatably engagable with the hub of a needle to draw the needle into the barrel after a fluid within the barrel has been expressed. U.S. Pat. No. 4,676,783 discloses an intravenous needle having a tube for receiving the needle upon retraction thereof. U.S. Pat. No. 4,692,156 illustrates and describes a hypodermic syringe having structure for engaging the piston with the needle to draw the needle into the barrel of the syringe after a fluid has been expressed from the syringe.

U.S. Pat. No. 4,693,257 describes a needle aspiration biopsy device having a needle translatable within a cylindrical sheath. U.S. Pat. No. 4,695,274 is directed to a jacket translatable posteriorly to expose the needle of a hypodermic syringe and anteriorly to relocate the needle therein; upon relocation, the needle is wiped to leave fluid and body substances outside the jacket.

After use, a single or a double ended needle assembly may contain, interiorly or exteriorly, a potentially infectious fluid or body substance which may drip, seep or otherwise come in contact with personnel, other equipment or a surface and pose a health hazard. Accordingly, any shields or guards used in conjunction with single or double ended needles must have the capability of not only preventing accidental needle stick but in maintaining body substance isolation after use.

SUMMARY OF THE INVENTION

A hub of a double ended needle used as part of a blood collection system includes a non-rotatably mounted axially translatable guard for receiving the anterior needle prior and subsequent to use. The guard is mounted upon the hub for retention at a first position prior to use and at a second position after posterior translation of the guard to exteriorize the anterior needle and for locking engagement with the hub at a third position after anterior translation of the guard to reenclose the anterior needle. A removable tab at the anterior end of the guard provides an aperture through which the needle is exteriorized and the tab includes means for plugging the aperture after the needle is lockingly enclosed within the guard to isolate any body substances therein. A posterior guard is non-rotatably mounted upon the hub to enclose and expose the posterior end of the hub and the posterior needle extending therefrom. In a single needle variant, the posterior needle is replaced by a luer lock for engaging the hub of a conventional syringe. The posterior guard is remounted posteriorly on the hub subsequent to use to isolate any body substances remaining at the posterior end of the hub from contact with a user.

It is therefore a primary object of the present invention to provide body substance isolation capability for needles used in medical practice.

Another object of the present invention is to provide a non-detachable guard for isolating any body substance residue attendant a hypodermic needle.

Yet another object of the present invention is to provide an axially translatable non-rotatable guard for maintaining sterile a hypodermic needle prior to use and for guarding against contact by a user of the hypodermic needle or by any body substance associated therewith after use.

Still another object of the present invention is to provide a non-detachable guard for a hypodermic needle which sealingly encloses from behind the point of a hypodermic needle after use.

A further object of the present invention is to provide guards for body substance isolation of both ends of a double ended hypodermic needle.

A yet further object of the present invention is to provide guards for body substance isolation of both ends of a single hypodermic needle detachably attachable to a syringe.

A still further object of the present invention is to provide a method for isolating body substances attendant a single ended hypodermic needle.

A still further object of the present invention is to provide a method for achieving body substance isolation after use of a hypodermic needle or syringe device.

These and other objects will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates a pair of guards for protecting a double ended needle;

FIG. 2 illustrates exposure of the posterior end of the double ended needle;

FIG. 3 illustrates translation of the guard attendant the anterior needle of the double ended needle;

FIG. 4 is a cross section of the cap attendant the anterior needle guard;

FIG. 5 is a side cross sectional view of the present invention;

FIG. 6 is a top cross sectional view of the present invention;

FIG. 7 is a cross sectional view taken along lines 7—7;

FIG. 8 is a cross sectional view taken along lines 8—8;

FIG. 9 is a cross sectional view taken along lines 9—9;

FIG. 10 is a partial cross sectional view showing the anterior needle ready for use;

FIG. 11 is a partial cross sectional view showing the enclosure of the anterior needle after use;

FIG. 12 illustrates a variant of the anterior guard retention mechanism;

FIG. 13 is a detailed view of a segment shown in FIG. 12;

FIG. 14 illustrates a partial cross sectional view of the anterior guard retention mechanism of the variant;

FIG. 15 illustrates attachment of an anterior guard to a collection tube holder;

FIG. 16 illustrates in partial cross section a configuration of the double ended needle having an internally mounted proximal guard;

FIG. 17 is a cross section taken along lines 17—17 in FIG. 16;

FIG. 18 illustrates the anterior guard and proximal guard in extended positions;

FIG. 19 is a perspective view of the proximal guard;

FIG. 20 is a perspective view of the hub of the double ended needle;

FIG. 21 illustrates an embodiment of the present invention usable in conjunction with a single ended needle;

FIG. 22 illustrates attachment of the single needle embodiment to the barrel of a hypodermic syringe;

FIG. 23 illustrates the present invention ready for use in conjunction with a hypodermic syringe;

FIG. 24 is a partial cross sectional view illustrating the attachment of the single needle with a hypodermic syringe;

FIG. 25 is an exploded view of a further variant of the present invention;

FIG. 26 is a partial cross sectional view illustrating the further variant shown in FIG. 25 after use;

FIGS. 27, 28 and 29 illustrate partial cross sectional views of the guard retention mechanism for the further variant shown in FIG. 25;

FIGS. 30 and 31 illustrate another embodiment of the guard retention mechanisms shown in FIGS. 25, 27, 28 and 29;

FIGS. 32, 33, 34 and 35 illustrate partial cross sectional views of a further embodiment of the locking mechanisms usable in conjunction with the further variant illustrated in FIG. 25.

DETAILED DESCRIPTION OF THE PREFERRED EMBODIMENT

Referring to FIG. 1, there is shown a double ended needle enclosed within an anterior guard 10 and a posterior guard 12. The junction therebetween is sealed with a band of conventional sealing tape 14. As the two guards and sealing tape are essentially impermeable, the double ended needle closed therein can be maintained sterile for an indeterminate period. The anterior guard includes a cap 16 having a tab 18 formed as part of the cap through a frangible boss 20. A plug 22 extends from the tab for sealingly engaging the aperture formed in cap 16 upon disengagement of boss 20 therefrom.

Anterior guard 10 and posterior guard 12 are predominantly oval or oblong in cross section to minimize rolling upon a surface and to prevent rotation of the guards relative to the longitudinal axis of the enclosed needle. Anterior guard 10 may include opposed flats 24 to assist in gripping the guard along with segmented grooves 26 to assist in a user gripping and manipulating the guard. Similarly, posterior guard 12 may include opposed flats 28 and grooves (not shown).

To expose the double ended needle for use, sealing tape 14 is removed and posterior guard 12 is translated posteriorly to expose hub 30 and the posterior needle enclosed within sheath 32. The posterior end of the hub includes a threaded section 34 for engagement with the threads attendant a blood collection tube holder (not shown). Thereafter, anterior guard 10 is griped to insert the posterior needle and sheath 22 within the blood collection tube holder and to attach hub 36 to the holder by means of threaded section 34. After attachment of the hub (the attachment is well known and is not shown for sake of clarity of illustration), tab 18 is gripped and twisted, or otherwise manipulated with respect to anterior guard 10 to sever boss 20 from the end of cap 16, as illustrated in FIG. 3. Upon severance, an aperture 38 is formed in the cap. This aperture permits exteriorization of anterior needle 40 from within anterior guard 10 upon posterior axial translation of the anterior guard.

FIG. 4 illustrates certain details attendant cap 16. The anterior end of anterior guard 10 may include a ramp 42 defining, in part, an annular depression 44. Cap 16 includes a radially inwardly oriented ramp 46 formed as part of skirt 48 to cooperatively engage with ramp 42 and guide cap 16 onto the anterior end of anterior guard 10. A lip 50 of ramp 46 drops into and is retained within depression 44 upon attachment of the cap to secure the cap to the anterior guard. The junction between cap 16 and anterior guard 10 may be a force fit to establish a seal therebetween; in addition, ultrasonic techniques or an adhesive may be employed to develope the point of attachment and seal. By employing a cap 16 to seal the anterior end of anterior guard 10, initial assembly of the anterior guard upon the double ended needle may be from the posterior end of the needle. Such assembly is preferred for reasons recited below.

It may be noted that FIG. 4 also illustrates sealing of aperture 38 after use of the double ended needle. After tab 18 has been severed, it is retained until use of the double ended needle has been completed. Thereafter, plug 22 of the tab is inserted within aperture 38. By suitable dimensioning, a force fit can be established to prevent leakage or seepage of any fluid or body substance associated with anterior needle 40.

Referring jointly to FIGS. 5 to 9, certain details attendant the structural and operational relationships between anterior guard 10, posterior guard 12 and double ended needle 36 will be described. Boss 20, in combination with cap 16 define a cavity 56 which produces a frangible skirt 58 of the boss. This skirt is ruptured upon application of a force to tab 18 relative to anterior guard 10; moreover, cavity 56, to the extent it is associated with cap 16, will define aperture 38 in order to ensure that such aperture is functionally dimensioned to cooperate with plug 22 and effect a seal therebetween. Hub 36 is generally oval in cross section in conformance with the cross section of anterior guard 10 and posterior guard 12. Tab 18 may have formed therein opposed depressions 52, 54 to reduce the mass thereof for manufacturing purposes and to provide a more sure grip of the tab by a user.

Hub 36 includes an anterior oval shaped flange 60. This flange serves a number of important functions. The interior dimension of anterior guard 10 tapers posteriorly; this requires the initial assembly of the anterior guard to be from the posterior end of the hub. As the anterior guard is moved from the retracted to the extended position (moved anteriorly), the fit between flange 60 and interior surface 61 of the anterior guard becomes more and more tight. The tight fit between the flange and the anterior guard serves as support for the anterior guard to reduce any tendency of the anterior guard to wobble when in the extended position. To permit the flange to conform with the reduced taper of the anterior guard resulting in compression of the flange, a plurality of slots 62 are formed therein, as illustrated in FIG. 9.

Hub 36 includes a piston 64 oval in cross section and conforming, generally, with the interior cross section of anterior guard 10. Because of the taper of the anterior guard, extension of the anterior guard will result in a tendency of the anterior guard to compress piston 64. Such compression establishes a tight fit therebetween to prevent seepage of any fluids or blood substances dripping from a otherwise discharged from needle 40 after use of the needle. It also prevents the likelihood of separation between the hub and the anterior guard. Accordingly, piston 64 precludes flow of body substances posteriorly toward hub 36 and the body substance becomes isolated within the anterior guard. Piston 64 also provides the function of a robust support for the anterior guard. The combination of support provided by flange 60 and piston 64 to the anterior guard helps assure against wobble of the anterior guard when the latter is in the extended position and against disengagement between the anterior guard and the hub.

Hub 36 includes a plurality of axially oriented ridges 66, 68, 70, 72, 74 and 76. These ridges are formed to reduce the mass of the hub and to facilitate certain manufacturing functions. Primarily, the ridges provide six axially oriented surface areas for supporting anterior guard 10 upon axial translation of the anterior guard with respect to hub 36. The posterior end of anterior guard 10 includes a radially inwardly oriented ridge 80, which ridge, in cooperation with hub 36, supports the posterior end of the anterior guard. In the first position of anterior guard 10, the position prior to use, ridge 80 is located adjacent a ramp 82 extending radially from each of axial ridges 66–76. These ramps discourage posterior translation of the anterior guard. However, the height of the ramps, in combination with the flexibility of the posterior end of the anterior guard permits translation of the anterior guard posteriorly therepast upon application of a modest force to the anterior guard. Upon such translation, the anterior guard is retracted to expose anterior needle 40. The posterior end of hub 36 includes a ramp 84 extending radially outwardly from each of ridges 66–76 and a lip 86 disposed upon each of the axial ridges and posteriorly displaced from ramps 84 by a space approximately equivalent to the width of annular ridge 80 of the anterior guard. Upon retraction of the anterior guard, ridge 80 is forced past ramps 84 into abutting relationship with lips 86. The effect of ramps 84 is that of discouraging annular ridge 80 from anterior movement therepast; they will cause anterior guard 10 to be selectively retained adjacent lips 86 in a second position corresponding to retraction of the anterior guard.

Upon extension of the anterior guard from the second position, annular ridge 80 will accommodate translation past ramps 84. Upon further anterior translation of anterior guard 10, side 88 of annular ridge 80 will abut sloping surface 90 of piston 64. Simultaneously, annular ridge 80 will become displaced within grooves 92 formed in each of axial ridges 66–76. Edge 94 of slots 92 is generally radially oriented to discourage posteriorly oriented movement of annular ridge 80 therepast. As discussed above, anterior guard 10 tapers posteriorly. Accordingly, extension of the anterior guard posteriorly will produce an increasingly tighter fit between the anterior guard and each of flange 60 and piston 64. This tight fit, and the friction resulting therefrom, in combination with the mechanical impediment presented by side 94 of slots 92 against annular ridge 80 will serve the function of locking the anterior guard in the third or extended position. To assist a user in translating the anterior guard, diametrically opposed grooves 26, with the corresponding ridges formed thereby, provide a sure gripping surface. Furthermore, flats 24, which may be roughened, provide a further gripping surface for a user.

As illustrated in FIG. 5, posterior guard 12 may be secured to anterior guard 10 in an overlapping relationship. To assist in retaining the posterior guard secured in place, a shallow groove 100 may be formed in the posterior end of the anterior guard for receiving a similarly shallow radially inwardly oriented mound 102.

Referring to FIG. 10, anterior guard 10 is shown in the second or retracted position with respect to hub 36. In this position, annular ridge 80 is disposed in slots 96 formed in ridges 66-76. Anterior needle 40 has been exteriorized through aperture 38 of cap 16. Although a collection tube holder would normally be threadedly engaged with threaded section 34, it is not shown for purposes of clarity and illustration of the relationship between the anterior guard and the hub.

In FIG. 11, anterior guard 10 is shown in the third or extended position with respect to hub 36. In this position, anterior needle 40 is fully enclosed within the anterior guard. Since it is not unusual for a fluid or body substance to be coated upon the needle or drip from the point of the needle, containment of such fluid or body substance must be assured. Aperture 38 has been closed by insertion of plug 22 extending from tab 18. Accordingly, seepage of fluid or body substance through the aperture is precluded. In the extended or third position, annular ridge 80 is lockingly disposed in slots 92 attendant hub 36, as described above. Both piston 64 and flange 60 have been slightly compressed due to the posterior tapering of the inner surface of the anterior guard. This compression, with the resulting tight fit between piston 64 and the interior surface of the anterior guard will prevent leakage or seepage of any fluid or any body substance form within the anterior guard therepast. Accordingly, any fluid or body substance attendant needle 40 will be isolated within the needle guard. It may also be noted that in the third or extended position of the anterior guard, it is stabilized by three annularly located and axially displaced points of support: flange 60, piston 64 and slots 92. Such multipoint support will maintain the anterior guard stably located with regard to hub 36 and wobble thereof is essentially precluded and the likelihood of disengagement therebetween is substantially reduced.

The use of a hub having a plurality of axially aligned ridges for supporting the anterior guard results in several advantages. First, manufacturing consideration attendant shrinkage, cooling and accuracy of the part formed are enhanced. Second, unnecessary weight, without jeopardizing structural stability, is eliminated. Third, less material is used which will reduce manufacturing costs. Fourth, control of and support for translation of a guard therealong is more readily definable and controllable than that of a hub of solid mass. Thus, a hub having a plurality of longitudinal ridges represents an advance in the state of the art.

The use of a hub having a plurality of axially aligned ridges for supporting the anterior guard results in several advantages. First, manufacturing considerations attendant shrinkage, cooling and accuracy of the part formed are enhanced. Second, unnecessary wait, without jeopardizing structural stability and weight, is eliminated. Third, control of and support for translation of a guard therealong is more readily definable and controllable than that of a hub of solid mass. Thus, a hub having a plurality of longitudinal ridges represents an advance in the state of the art.

Referring jointly to FIGS. 12, 13 and 14, there is shown a variant of the hub and a variant of the means for retaining the anterior guard in the first, second and third positions. Certain other features to comport therewith have also been modified. Specifically, hub 112 is essentially cylindrical in cross section. It includes an annularly expanded cylindrical section 114 and a truncated cone shaped segment 116. Anterior guard 118 includes a radially inwardly extending ridge 120 at the posterior end of the anterior guard. In the first position of the anterior guard, ridge 120 is disposed in a channel 122 formed intermediate annular ring 124 and annular ring 126. The second position of anterior guard 118 is defined by an annular ring 128 disposed about hub 112 at the posterior end portion thereof. Upon posterior translation of anterior guard 118, ridge 120 will abut ring 128 and the ring prevents further translatory movement of the anterior guard therepast; it also defines the second position of the anterior guard, as particularly illustrated in FIG. 14. The third position of the anterior guard is defined by channel 130 disposed intermediate ring 126 and section 114. To discourage posterior displacement of the anterior guard posteriorly when it is in the third position, ring 126 may extend radially outwardly more than that of ring 124 to provide a greater impediment against passage of ridge 120 thereover.

The interior of the annular guard includes a cone shaped band 132 force fitable with segment 116 upon translation of the anterior guard to the third position. Accordingly, a sealed engagement between the inner surface and the anterior guard and segment 116 of hub 122 is established to prevent flow therepast of any fluid or body substance which might flow or drip from anterior needle 134. As discussed above, a cap 16 and tab 18 is attached to the anterior end of anterior guard 118 to provide an initially sealed and after use sealable anterior end. This sealed anterior end of the anterior guard will preclude flow or seepage of any fluid or body substance that might drip or otherwise be dispensed from needle 134. Grooves 26 may be disposed along opposed sides of the anterior guard to assist in manipulating the guard to obtain translatory movement thereof.

The needle illustrated with respect to variant 110 is a double ended needle usable primarily with a blood collection holder (not shown). Such a holder is threadedly engaged with threaded section 34 to penetrably receive needle 136 disposed within but extentable from sheath 32. As is well known, sheath 32 collapses axially upon insertion of needle 136 through the stopper of a collection tube placed within the collection tube holder. It is to be noted that with respect to variant 110, a posterior guard, such as guard 12 shown in FIGS. 5 and 6, is attachable to anterior guard 118 in an overlapping relationship adjacent edge 138 and cylindrical surface 140 (See FIG. 14).

Collection tube holders, used in conjunction with double ended needles, are generally reused. Such reuse sometimes tends to wear the female threads disposed in the hub or boss of the collection tube holder. If the wear is sufficient or if the threaded engagement is not firm, disengagement of the double ended needle from the collection tube holder may occur. Such unexpected and unwanted disengagement may cause spillage of the blood, or other fluid being collected. To ensure against such inadvertent disengagement, a variant of the above-described anterior guard 10 may be employed, as illustrated in FIG. 15. Anterior guard 10 includes radially inwardly oriented ridge 80 at the posterior end thereof. The above-described corresponding ramp 84, lip 86 and slot 96 in hub 30 shown in FIG. 16 are eliminated in this variant. Such elimination permits posterior translation of the anterior guard commensurate with engagement of the anterior end of the guard with the anterior end of hub 30. Collection tube holder 141 includes a boss 142 having a threaded passageway 143 disposed therein for threadedly engaging hub 30 of double ended needle 36.

The exterior surface of boss 142 defines an oval in cross section, commensurate with the internal cross section of anterior guard 10, as illustrated in FIG. 7. Such cross section of the boss permits penetrable engagement of the boss with the anterior guard upon posterior translation of the anterior guard to the position illustrated in FIG. 15. The boss also includes a groove 144 extending thereabout for receiving ridge 80 of anterior guard 10. The capture of the ridge within the groove, in combination with a certain resiliency of the anterior guard, will tend to retain the anterior guard in locking engagement with boss 142.

Because of the oval cross section of double ended needle 36 in combination with the oval cross section of anterior guard 10, rotation therebetween about the respective longitudinal axis is mechanically precluded. The oval cross section of boss 142, in combination with capture of anterior guard 10 therewith, will preclude rotation intermediate the boss and the anterior guard. Disengagement of the double ended needle from the collection tube holder requires rotation therebetween to effect threaded disengagement. Since such rotation is precluded by the engagement between boss 142 and anterior guard 10, such threaded disengagement between the double ended needle and the collection tube holder is precluded.

In the event double ended needle 36 is circular in cross section and anterior guard 10 is commensurately cross sectioned, boss 142 must be cylindrically shaped. Engagement of anterior guard 10 with hub 142, under such circumstances and as illustrated in FIG. 15, will not preclude rotation between the double ended needle and the collection tube holder. However, relative rotation therebetween may be impeded by dimensioning the anterior guard in such manner that the anterior end or cap thereof engages the anterior end of hub 30 upon engagement of ridge 80 with groove 144. With such arrangement, any tendency for inadvertent rotation of the double ended needle with respect to the collection tube holder which might result in anterior translation of the double ended needle would be resisted by the anterior end of the anterior guard. Thereby, threaded disengagement between the collection tube holder and the double ended needle would be restrained.

An internally mounted proximal guard 146 extendable from hub 30 is illustrated in FIG. 16. The proximal guard may include a ramp 84 lip 86 and slot 96, as described above, to receive ridge 80 of anterior guard 10. Proximal guard 146 includes a radially inwardly oriented ridge 147 to be retainingly received within a groove 148 disposed about hub 30, as particularly illustrated in FIG. 18. It may be appreciated that by suitable dimensioning of proximal guard 146 in combination with the interior surface of anterior guard 10, ridge 147 is restrained from disengaging with groove 148 when the anterior guard overlaps the proximal guard. Accordingly, upon such overlap, the proximal guard is precluded from axial displacement.

Upon anterior translation of anterior guard 10, as particularly illustrated in FIG. 18, proximal guard 146 can be translated posteriorly along hub 30 to enclose therein posterior needle 136 and a sheath 32 extending thereabout, if used. Hub 30 includes a slot 149 extending about the posterior end of the hub for receivingly engaging ridge 147 upon posterior translation of the proximal guard. As particularly illustrated in FIG. 19, the proximal guard may include a plurality of resilient fingers 151 to permit accommodation of ridge 147 into and out of groove 148 and slot 149. As particularly illustrated in FIG. 20, groove 148 may be disposed solely upon the upper and lower parts of hub 30. It is to be understood that the groove may be segmented and extend across each of the ridges of the hub for engagement with commensurate parts of ridge 147 in the proximal guard. Similarly, slots 149 may be disposed solely upon the upper and lower parts of the hub although the slots may be, in segmented form, extended about the hub. As particularly illustrated in FIG. 17, proximal guard 146 is generally oval in cross section to mate with the hub and the anterior guard. However, the proximal guard may be circular in configuration or of other cross section commensurate with the cross sections of a hub and an anterior guard with which it may be used.

A single needle embodiment of the present invention is illustrated in FIGS. 21-24. Anterior guard 150 and attached tab 152 are functionally and structurally virtually equivalent with anterior guard 10 and tab 18. Similarly, posterior guard 154 is virtually the equivalent of posterior guard 12. Sealing tape 156 may be secured at the junction of the anterior and posterior guards to maintain the enclosed needle sterile. The single ended needle 160, as partially shown in FIG. 22, includes a hub 162 which may have opposed flats 164 and the cross section of the hub may be generally oblong, as illustrated, to discourage rolling upon a surface. The posterior end of hub 162 includes a conventional luer lock mechanism 166 for engagement with an internally threaded shroud 168 extending from the anterior end of a barrel 170 of a syringe 172. As is conventional, a hollow cone 174 extends from barrel 170 for mating sealed engagement with an equivalently configured passageway within the posterior end of hub 160.

After removal of posterior guard 154, hub 162 on anterior guard 150 may be grasped to mate it with syringe 172 by mating luer lock 166 with threads 176 disposed within shroud 168, as shown in FIG. 18. Thereafter, tab 152 is separated from anterior guard 150 to develope aperture 178. Upon rearward axial translation of the anterior guard, it will be repositioned to it's second position, as described in further detail with respect to the configuration shown in either FIG. 5 or FIG. 12. In the second position, as illustrated in FIG. 23, anterior needle 180 is exteriorized from cap 182 and ready for use upon operation of syringe 172. The anterior guard is retained in place, as discussed above with respect to FIGS. 10 or 14. It may be noted that translation of the anterior guard is from a location posterior of the point of needle 180 to avoid possibility of inadvertent needle stick. After use of needle 180, anterior guard 150 is translated anteriorly, also from a possession posterior of the point of the needle. Such translation will result in relocation of the anterior guard in the third position, as illustrated in FIG. 11. Thereafter, plug 184 of tab 150 is inserted within aperture 178 to seal it. For reasons discussed above, relocation of anterior chamber 150 in the third position will provide body substance isolation within the anterior guard.

As is evident from the above discourse and inspection of the figures discussed, anterior translation of the guard past the anterior end the hub is precluded due to the interference between the anterior guard and the hub. This interference requires that the guard be initially mounted upon the hub from its posterior end before the cap is attached to the guard. Such methodology for assembling either single ended or double ended needles is believed to be an advance in the state of the art.

Referring to FIG. 25, there is shown a further variant 190. It includes a hub 192, which may be similar to hub 112 shown in FIG. 12. A posterior guard 194 is usable to cover and shield posterior needle 196 of the double ended needle extendign from hub 192. An anterior guard 198 shields anterior needle 200 prior to and after use. The needle includes a stopper 202 from which a frangible cap 203 extends. Referring jointly to FIGS. 25 to 29, certain features attendant anterior guard 198 will be described in detail. A pair of ridges 204 and 206 extend annularly about the posterior end of hub 192 to define a channel 208, which channel locates the second position of anterior guard 198. A ramp 210, in combination with an annular ridge 212 defines an annular channel 214. An annular sidewall 216, in combination with ridge 212 defines a further channel 218.

Anterior guard 198 includes a skirt 220 disposed at the posterior end of the anterior guard. It includes a plurality of longitudinally oriented tangs 222 defined by slits 224, as particularly shown in FIG. 25. In FIG. 26, each tang includes a radially inwardly extending flange 226 having a radially oriented sidewall 228 terminating at a point 230 of the flange.

In the first position of anterior guard 198 (FIG. 27), flange 226 rests within channel 214. After cap 203 is broken off from stopper 202, the anterior guard may be axially translated posteriorly. As illustrated in FIG. 28, continuing translation of the anterior guard will locate it in the second position, as defined by flange 226 resting within channel 208. In this position of the anterior guard, needle 200 has been exteriorized through aperture 232 formed within stopper 202. After the needle has been used, anterior guard 198 is axially translated anteriorly to the extent that flange 226 has been located past channel 214 and into channel 218. Further anterior movement of the anterior guard is precluded by interference between sidewall 228 of the flange and sidewall 216 of hub 192 (See FIG. 29). Posterior translation of the anterior guard is restrained by ridge 212. To prevent an outflow of any fluid or body substance from or about needle 200, cap 203 may be lodged within aperture 232.

Posterior guard 194 encloses threaded section 234 from which a posterior needle 236 extends. As described above, section 234 is intended for mating with a collection tube holder. A sheath 238, as described above, is mounted in cooperating relationship with posterior needle 236.

Referring jointly to FIGS. 30 and 31 there is illustrated a variant of skirt 220 shown in FIGS. 25 to 29. Herein, skirt 240 defines a cylindrical section having a continuous radially inwardly and anteriorly oriented flange 242 extending from the posterior end of the skirt. This flange serves the same function as flanges 226 extending from tangs 222 of variant 190. That is, they cooperate with the corresponding positioning elements of hub 192 to locate anterior guard 244 with respect to the hub in each of the first, second and third positions.

Referring jointly to FIGS. 32, 33, 34 and 35 a yet further variant of the mechanism for securing an anterior guard 250 upon a hub 252 will be described. An annular ridge 254, in combination with an annular flange 256 define a channel 258. An annular skirt 260, defining an internal cone shaped annular surface 262 is displace anteriorly of flange 256. A convoluted annular ridge 264 exends radially inwardly from anterior guard 250.

Upon initial assembly of anterior guard 250, the guard is translated posteriorly of needle 266 to enclose it therein. Upon contact of convoluted ridge 264 with skirt 260, the skirt will be bent radially inwardly and the convoluted ridge will be bent radially outwardly. Upon further translation of the anterior guard, the convoluted ridge will extend radially inwardly and become seated within channel 258, as illustrated in FIG. 34. This is the above-described first position of the anterior guard. Upon further translation of the anterior guard posteriorly, convoluted ridge 264 will be compressed/bent sufficiently to override ridge 254. At the posterior end of the hub, there will be located a further ridge which serves as an impediment or stop to further posterior translation of the anterior guard. This is the above-described second position of the anterior guard. Upon anterior translation of the anterior guard, convoluted ridge 264 will be forced over ridge 254 and ridge 256 until it comes to rest within channel 268 disposed between ridge 256 and skirt 260, as illustrated in FIG. 35. The interference between the convoluted ridge and the skirt will preclude further anterior translation of anterior guard 250. Thereafter, an aperture 268 formed in the anterior end of the anterior guard to permit exteriorization of needle 266 may be plugged by one of the above described elements.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirement without departing from those principles.

We claim:

1. A guard for enclosing a needle extending from a hub before and after use to prevent inadvertent needle stick and to provide body substance isolation, said guard comprising in combination:
   (a) means for locating said guard relative to the hub in a first position to enclose the needle within said guard;
   (b) means for posteriorly relocating said guard to and for urging retention of said guard in a second position relative to the hub to exteriorize the needle from within said guard;
   (c) means for anteriorly repositioning said guard for locking said guard in a third position relative to the hub to reenclose the needle within said guard; and
   (d) means for isolating within said guard any body substances attendant the needle and within upon repositioning of said guard into the third position, said isolating means including means for sealing the posterior end of said guard about the hub, said sealing means comprising a piston associated with the hub and taper means disposed at the junction of said piston and said guard upon location of said guard in the third position for developing a seal at the junction between said piston and said guard.

2. The guard as set forth in claim 1 wherein said isolating means includes at least two axially displaced points of support between said guard and the hub, one of said support points being said piston.

3. The guard as set forth in claim 2 wherein the other of said support points comprises a compressible flange secured to the hub for supporting the interior of said guard.

4. The guard as set forth in claim 1 wherein said guard includes radially inwardly extending means for supporting said guard upon the hub and means disposed in said hub for releasably capturing said supporting means when said guard is in the first and second positions.

5. The guard as set forth in claim 4 including means disposed in said hub for lockingly capturing said supporting means when said guard is in the third position.

6. The guard as set forth in claim 1 wherein said isolating means includes a tab disposed at the anterior end of said guard for enclosing the anterior end of said guard prior to use of the needle and for developing an aperture in the anterior end of said guard.

7. The guard as set forth in claim 6 wherein said tab includes a frangible boss for developing the aperture.

8. A guard for enclosing a needle extending from a hub before and after use to prevent inadvertent needle stick and to provide body substance isolation, said guard comprising in combination:
(a) means for locating said guard relative to the hub in a first position to enclose the needle within said guard;
(b) means for posteriorly relocating said guard to and for urging retention of said guard in a second position relative to the hub to exteriorize the needle from within said guard;
(c) means for anteriorly repositioning said guard for locking said guard in a third position relative to the hub to reenclose the needle within said guard; and
(d) means for isolating within said guard any body substances attendant the needle and within upon repositioning of said guard into the third position, said isolating means including a tab disposed at the anterior end of said guard for closing the anterior end of said guard prior to use of the needle and for developing an aperture in the anterior end of said guard, said tab including a frangible boss for developing the aperture and a plug for sealing the aperture subsequent to use of the needle.

9. The guard as set forth in claim 1 wherein the needle is a double ended needle having an anterior needle and a posterior needle extending from opposed ends of said hub, said guard being associated with the anterior needle and including a second guard for enclosing the posterior needle before and after use of the double ended needle.

10. The guard as set forth in claim 9 including means for releasably attaching said second guard to said guard in overlapping relationship.

11. The guard as set forth in claim 10 including means for sealing the junction between said guard and said second guard.

12. A method for preventing inadvertent needle stick by a needle extending from a hub and for providing body substance isolation within a needle enclosing guard after use of the needle, said method comprising the steps of:

(a) locating the guard anteriorly relative to the hub in a first position to enclose the needle within the guard;
(b) relocating the guard posteriorly relative to the hub and urging retention of the guard in a second position to exteriorize the needle from the guard;
(c) repositioning the guard anteriorly relative to the hub to lock the guard in a third position to reenclose the needle within the guard; and
(d) isolating within the guard any body substances attendant the needle upon repositioning the guard in the third position, said step of isolating including the step of sealing the junction between the guard and the hub.

13. The guard as set forth in claim 12 wherein the hub supports a double ended needle extending anteriorly and posteriorly of the hub and wherein the guard recited in said steps of locating, relocating and repositioning cooperates with the anteriorly extending needle and including the step of releasable locating a further guard relative to the hub to enclose the posteriorly extending needle.

14. The method as set forth in claim 13 wherein said step of isolating includes the step of securing the guard with the further guard.

15. The guard as set forth in claim 14 wherein said step of isolating includes the step of securing the sealing tape about the junction of the first guard and the second guard.

16. The guard as set forth in claim 9 including means extending from said hub for selectively shielding the posterior needle, said shielding means being extendable posteriorly of said hub subsequent to anterior repositioning of said guard.

17. The guard as set forth in claim 1 wherein the hub includes means for engaging a collection tube holder and means for retaining the hub with the collection tube holder, said engaging means being independent of but operable in conjunction with said retaining means.

18. The guard as set forth in claim 12 wherein the hub includes an anterior needle and a posterior needle and including the step of selectively shielding the posterior needle by extending a shield posteriorly from the hub.

19. The guard as set forth in claim 12 wherein the hub includes means for engaging a blood collection tube and including the step of retaining the hub engaged with the blood collection tube independent of the engaging means.

20. The guard as set forth in claim 19 wherein the hub includes an anterior needle and a posterior needle and including the step of selectively shielding the posterior needle by extending a shield posteriorly from the hub.

21. The guard as set forth in claim 9 wherein the hub includes means for engaging a collection tube holder and means for retaining the hub with the collection tube holder, said engaging means being independent of but operable in conjunction with said retaining means.

* * * * *